(12) United States Patent
Lyytikäinen et al.

(10) Patent No.: US 10,583,035 B2
(45) Date of Patent: Mar. 10, 2020

(54) INSERTER

(71) Applicant: Bayer Oy, Turku (FI)

(72) Inventors: Heikki Lyytikäinen, Naantaki (FI); Ilkka Jutila, Suavo (FI); Ulla Calvo Alonso, Piispanristi (FI); Harri Jukarainen, Kuusisto (FI); Taina Tjäder, Littoinen (FI); Andrew Macleod, Cambridge (GB); Michael Noble, London (GB); David Whitaker, Harringay (GB)

(73) Assignee: Bayer Oy, Turku (FI)

( * ) Notice: Subject to any disclaimer, the term of this patent is extended or adjusted under 35 U.S.C. 154(b) by 342 days.

(21) Appl. No.: 15/647,104

(22) Filed: Jul. 11, 2017

(65) Prior Publication Data

US 2018/0014966 A1  Jan. 18, 2018

Related U.S. Application Data

(60) Division of application No. 14/590,969, filed on Jan. 6, 2015, now Pat. No. 9,707,123, which is a
(Continued)

(30) Foreign Application Priority Data

Sep. 17, 2008 (FI) ...................................... 20080524

(51) Int. Cl.
*A61F 6/18* (2006.01)
*A61F 6/14* (2006.01)

(52) U.S. Cl.
CPC ................ *A61F 6/18* (2013.01); *A61F 6/142* (2013.01)

(58) Field of Classification Search
CPC ...................................................... A61F 6/18
(Continued)

(56) References Cited

U.S. PATENT DOCUMENTS

| 3,533,406 A | 10/1970 | Tatum |
| 3,656,483 A | 4/1972 | Rudel |

(Continued)

FOREIGN PATENT DOCUMENTS

| CA | 1033247 | 6/1978 |
| CN | 1377635 | 11/2002 |

(Continued)

OTHER PUBLICATIONS

USPTO, Non-Final Office Action for U.S. Appl. No. 13/119,401, dated Aug. 17, 2012, 11 pages.
(Continued)

*Primary Examiner* — Tarla R Patel
(74) *Attorney, Agent, or Firm* — IP Spring

(57) ABSTRACT

The present invention relates to an inserter for an intrauterine system, comprising a handle (3) having a longitudinal opening (8) at its first end, said opening (8) having a longitudinal axis parallel to the longitudinal axis of the inserter, a first end (8 *a*) and a second end (8 *b*), a movable slider (5) arranged in said longitudinal opening (8) and having a first end (5 *a*) and a second end (5 *b*), a plunger (2) attached to the handle (3) and having a longitudinal axis, and an insertion tube (6) having a first end, a second end and a longitudinal axis essentially parallel to the longitudinal axis of the plunger (2), the insertion tube (6) being, along said longitudinal axis, movably arranged around the plunger (2). The invention is characterised in that it further comprises a flange (4) arranged on the insertion tube (6) at its first end, and means for locking the slider (5) into a position showing the correct insertion depth for the intrauterine system, said means being adjustable with respect to the opening (8) of the handle.

6 Claims, 11 Drawing Sheets

Related U.S. Application Data continuation of application No. 13/857,134, filed on Apr. 4, 2013, now abandoned, which is a continuation of application No. 13/119,399, filed as application No. PCT/FI2009/050733 on Sep. 11, 2009, now abandoned.

(58) Field of Classification Search
USPC ............. 128/840, 839, 834, 830; 604/48, 19
See application file for complete search history.

(56) References Cited

U.S. PATENT DOCUMENTS

| | | | |
|---|---|---|---|
| 3,783,861 A * | 1/1974 | Abramson | A61F 6/18 |
| | | | 128/840 |
| 3,794,025 A | 2/1974 | Lerner | |
| 3,896,819 A | 7/1975 | Zaffaroni et al. | |
| 3,902,483 A | 9/1975 | Place et al. | |
| 3,918,444 A | 11/1975 | Hoff et al. | |
| 4,143,656 A * | 3/1979 | Holmes | A61F 6/18 |
| | | | 128/840 |
| 4,341,728 A | 7/1982 | Robertson et al. | |
| 4,353,363 A | 10/1982 | Sopena | |
| 4,413,985 A | 11/1983 | Wellner et al. | |
| 4,562,835 A | 1/1986 | Anderson | |
| 4,578,075 A | 3/1986 | Urquhart et al. | |
| 4,578,076 A | 3/1986 | Luukkainen et al. | |
| 4,678,463 A | 7/1987 | Millar | |
| 4,721,105 A * | 1/1988 | Wildemeersch | A61F 6/144 |
| | | | 128/840 |
| 4,724,832 A | 2/1988 | Strubel et al. | |
| 4,805,628 A | 2/1989 | Fry et al. | |
| 4,949,732 A | 8/1990 | Spoon et al. | |
| 5,146,931 A | 9/1992 | Kurz | |
| 5,217,450 A | 6/1993 | Pryor et al. | |
| 5,224,493 A | 7/1993 | Sawan et al. | |
| 5,370,129 A | 12/1994 | Diaz et al. | |
| 5,494,047 A | 2/1996 | Van Os | |
| 5,785,053 A * | 7/1998 | Macandrew | A61F 6/18 |
| | | | 128/840 |
| 6,056,976 A | 5/2000 | Markkula et al. | |
| 6,103,256 A | 8/2000 | Nabahi | |
| 6,119,696 A | 9/2000 | Turin | |
| 6,278,057 B1 | 8/2001 | Avellanet | |
| 6,299,027 B1 | 10/2001 | Berge et al. | |
| 6,588,429 B1 | 7/2003 | Wildemeersch | |
| 6,652,548 B2 | 11/2003 | Evans et al. | |
| D525,705 S | 7/2006 | Luukkainen | |
| 7,252,839 B2 | 8/2007 | Hallinen et al. | |
| 7,294,135 B2 | 11/2007 | Stephens et al. | |
| 7,926,488 B2 | 4/2011 | Luukkainen | |
| 2004/0261799 A1 | 12/2004 | Mock | |
| 2005/0178391 A1 | 8/2005 | Wildemeersch | |
| 2007/0056591 A1 | 3/2007 | McSwain | |
| 2007/0129734 A1 | 6/2007 | Jutila | |
| 2009/0123522 A1 | 5/2009 | Browning | |
| 2010/0168563 A1 | 7/2010 | Braver | |
| 2010/0186750 A1 | 7/2010 | Tran et al. | |
| 2010/0280464 A1 | 11/2010 | De Graaff et al. | |
| 2011/0017219 A1 | 1/2011 | De Graaff et al. | |
| 2011/0056501 A1 | 3/2011 | Kortesuo et al. | |
| 2011/0061659 A1 | 3/2011 | Cruzada et al. | |
| 2011/0146693 A1 | 6/2011 | Duesterberg et al. | |
| 2011/0162656 A1* | 7/2011 | Jutila | A61F 6/142 |
| | | | 128/830 |
| 2011/0166508 A1 | 7/2011 | Lyytikainen et al. | |
| 2011/0172593 A1 | 7/2011 | Lyyikäinen et al. | |
| 2011/0226257 A1 | 9/2011 | Lowe et al. | |

FOREIGN PATENT DOCUMENTS

| | | |
|---|---|---|
| CN | 201042478 | 4/2008 |
| DE | 8712168 | 10/1987 |
| DE | 29819558 | 2/1999 |
| DE | 19815552 | 9/1999 |
| DE | 29919662 | 3/2000 |
| EP | 0191957 | 8/1986 |
| EP | 0798999 | 10/1997 |
| EP | 0948948 | 10/1999 |
| EP | 1691740 | 8/2006 |
| FI | 882466 | 11/1999 |
| FI | 0080523 | 9/2008 |
| GB | 1039011 | 8/1966 |
| GB | 1403393 | 8/1975 |
| GB | 1486994 | 9/1977 |
| GB | 1543841 | 4/1979 |
| JP | 2010-510444 | 4/2010 |
| NL | 8601570 | 1/1988 |
| RU | 1377063 | 2/1988 |
| WO | 1995/028901 | 11/1995 |
| WO | 1996/018365 | 6/1996 |
| WO | 1996/029026 | 9/1996 |
| WO | 1999/005958 | 2/1999 |
| WO | 2000/000550 | 1/2000 |
| WO | 2001/013832 | 3/2001 |
| WO | 2003/017971 | 3/2003 |
| WO | 2005/048893 | 6/2006 |
| WO | 2007/075086 | 7/2007 |

OTHER PUBLICATIONS

USPTO, Non-Final Office Action for U.S. Appl. No. 13/771,066, dated May 22, 2013, 10 pages.
USPTO, Final Office Action for U.S. Appl. No. 14/088,329, dated Jan. 30, 2015, 18 pages.
USPTO, Non-Final Office Action for U.S. Appl. No. 14/088,329, dated Apr. 9, 2014, 19 pages.
USPTO, Non-Final Office Action for U.S. Appl. No. 14/088,329, dated Dec. 3, 2015, 19 pages.
USPTO, Non-Final Office Action for U.S. Appl. No. 13/857,134, dated Jul. 7, 2014, 19 pages.
USPTO, Non-Final Office Action for U.S. Appl. No. 13/119,397, dated Nov. 19, 2013, 19 pages.
EPO, Notice of Opposition for European Patent No. EP2352470, Sep. 26, 2013, 19 pages.
USPTO, Non-Final Office Action for U.S. Appl. No. 14/590,969, dated Jan. 29, 2016, 20 pages.
USPTO, Final Office Action for U.S. Appl. No. 13/119,397, dated Jan. 12, 2016, 21 pages.
USPTO, Non-Final Office Action for U.S. Appl. No. 13/119,399, dated Oct. 4, 2012, 22 pages.
USPTO, Non-Final Office Action for U.S. Appl. No. 13/119,397, dated May 5, 2015, 23 pages.
EPO, Reply to the Notice of Opposition to European Patent No. EP2352470, Apr. 25 2014, 28 pages.
USPTO, Final Office Action for U.S. Appl. No. 13/119,397, dated Sep. 5, 2014, 28 pages.
International Bureau of WIPO, International Preliminary Report on Patentability for International Patent Application No. PCT/FI2009/050733, dated Mar. 22, 2011, 6 pages.
International Bureau of WIPO, International Preliminary Report on Patentability for International Patent Application No. PCT/FI2009/050735, dated Mar. 22, 2011, 6 pages.
EPO, International Search Report and Written Opinion for International Patent Application No. PCT/FI2009/050735, dated Dec. 10, 2009, 8 pages.
EPO, International Search Report and Written Opinion for International Patent Application No. PCT/FI2009/050733, dated Dec. 23, 2009, 8 pages.
Johnson, et al., "Insertion and Removal of Intrauterine Devices," American Family Physician, vol. 71, No. 1, Jan. 1, 2005, pp. 95-102.
USPTO, Notice of Allowance for U.S. Appl. No. 14/590,969, dated Mar. 8, 2017, 10 pages.
USPTO, Notice of Allowance for U.S. Appl. No. 13/119,397, dated Apr. 5, 2017, 12 pages.
USPTO, Final Office Action for U.S. Appl. No. 14/590,969, dated Jul. 20, 2016, 14 pages.

(56) References Cited

OTHER PUBLICATIONS

USPTO, Ex Parte Quayle Action for Design U.S. Appl. No. 29/558,312, filed Feb. 6, 2017, 16 pages.
USPTO, Notice of Allowance for Design U.S. Appl. No. 29/558,312, dated Mar. 8, 2017, 5 pages.
USPTO, Non-Final Office Action for U.S. Appl. No. 15/245,042, dated Oct. 11, 2016, 6 pages.
USPTO, Non-Final Office Action for U.S. Appl. No. 15/470,870, dated May 23, 2017, 7 pages.
USPTO, Notice of Allowance for U.S. Appl. No. 15/245,042, dated Feb. 10, 2017, 8 pages.
USPTO, Notice of Allowance for U.S. Appl. No. 15/470,870, dated Nov. 8, 2017, 25 pages.
USPTO, Notice of Allowance for U.S. Appl. No. 14/088,329, dated May 18, 2016, 8 pages.
USPTO, Notice of Allowance for U.S. Appl. No. 15/891,187, dated Jun. 21, 2019, 8 pages.
USPTO, Non-final Office Action for U.S. Appl. No. 15/589,789, dated May 29, 2019, 17 pages.
USPTO, Non-final Office Action for U.S. Appl. No. 15/891,187, dated Nov. 2, 2018, 9 pages.
USPTO, Notice of Allowance for U.S. Appl. No. 15/891,187, dated Oct. 9, 2019, 8 pages.
USPTO, Non-final Office Action for U.S. Appl. No. 15/589,789, dated Dec. 30, 2019, 17 pages.

* cited by examiner

INSERTER

CROSS-REFERENCE TO RELATED APPLICATIONS

This application is a divisional of U.S. patent application Ser. No. 14/590,969, filed Jan. 6, 2015, which is a continuation of U.S. patent application Ser. No. 13/857,134, filed Apr. 4, 2013 (now abandoned), which is a continuation of U.S. patent application Ser. No. 13/119,399, filed Mar. 16, 2011 (now abandoned), which is a U.S. national phase application of International Patent Application No. PCT/FI2009/050733, filed Sep. 11, 2009, which claims priority to Finnish Patent Application No. 20080524, filed Sep. 17, 2008, the contents of all of which are incorporated herein by reference in their entirety.

The present invention is related to an inserter for positioning an intrauterine device or an intrauterine system in the uterus.

BACKGROUND OF THE INVENTION

Various types of inserters have been developed for the positioning of mechanical and copper wire-containing intrauterine devices (IUDs) as well as of intrauterine systems having a drug containing cylinder (IUSs). In the following, IUD and IUS can be used interchangeably and when one is mentioned, it is to be understood that either of them can be used.

Most common inserters are constructed for introducing the device into the uterus in a contracted state. These inserters usually comprise an insertion tube having a relatively narrow diameter and a rounded, blunt end which will pass through the cervical canal easily and will not damage or injure the fundus upon contact therewith, and a plunger inside the insertion tube. Prior to insertion the device, whether an IUD or an IUS, is usually retracted into the insertion tube either by means of string(s) attached to the device and intended for the removal of the device from the uterus, or by pushing the device into the insertion tube by a plunger with inserters having a special window to adapt the device in the expanded shape (see for example GB 1 403 393). Then the insertion tube with the device therein is introduced through the cervical canal into the uterus. When the device is correctly positioned, it is released either by pushing the plunger towards the uterus or by holding the plunger steady and by retracting the insertion tube outwards. Once expulsed from the insertion tube within the uterine cavity, the device is supposed to resume its original expanded shape.

Simple rod-shaped inserters have been suggested for inserting relatively small or sufficiently flexible intrauterine devices in their original, expanded shape by using simple push-in technique. With these inserters the correct positioning and a secure attachment of an IUS or IUD on the inserter as well as a proper handling of the removal strings may be difficult. Therefore there is still need for an improved inserter.

European patent application EP1 691 740 relates to an inserter, with which the correct positioning and directional stiffness of the device in the inserter prior to and during insertion can be ensured, for instance, by shaping the forward end of the plunger such that the IUS assumes a specified constant configuration when drawn into the insertion tube. The IUS thus will not be twisted during insertion.

European patent EP 798 999 relates to an inserter, which allows the correct positioning of an IUS also in those cases in which the elongate member of a T-shaped device contains active material, which involves a diameter larger than that of an elongate member of a copper-wire IUD. The inserter comprises a plunger, a handle attached to the plunger, a string for the removal of the IUS, a cleft on the end of the handle to lock the string(s) in such a way that the IUS remains immobile in relation to the plunger, and an insertion tube around the plunger. The IUS is drawn into the insertion tube by pushing the tube over the device or by pulling on the removal threads where after the threads are manually locked in the cleft. The relative movement of the plunger and the protective tube is restricted by a stop member or stop members to ascertain that the correct configuration of the IUS is achieved. The stop members ensure that the front edge of the insertion tube is stopped in a configuration in which the hemispherical tips of the T-wings remain partly uncovered by the insertion tube but the wings nevertheless remain pressed against each other. These stop members are however fixed on the handle.

The inserters described in these documents overcome many of the problems encountered with the conventional inserters, but the string(s) still need to be handled and manually locked. Further, the inserters are designed primarily for the insertion of the conventional devices which are to be inserted in a compressed configuration. Therefore there is still need for an improved inserter, which can be used to insert in original expanded configuration intrauterine devices and systems having frames of various shapes.

OBJECT AND SUMMARY OF THE INVENTION

An object of the invention is to provide a simple, easy to use inserter for the positioning of an intrauterine system in the uterus by solving at least partially at least some of the problems mentioned above. An object of the invention is particularly to provide an inserter having an improved system for securing the simple and correct positioning of the intrauterine system in the uterus.

A typical inserter for an intrauterine system according to the present invention, comprises a handle having a longitudinal opening at its first end, said opening having a longitudinal axis parallel to the longitudinal axis of the inserter, a first end and a second end, a movable slider arranged in said longitudinal opening and having a first end and a second end, a plunger attached to the handle and having a longitudinal axis, an insertion tube having a first end, a second end and a longitudinal axis essentially parallel to the longitudinal axis of the plunger, the insertion tube being, along said longitudinal axis, movably arranged around the plunger, a flange arranged on the insertion tube at its first end.

The inserter is characterized in that it further comprises means for locking the slider into a position showing the correct insertion depth for the intrauterine system, said means being adjustable with respect to the opening of the handle.

DETAILED DESCRIPTION OF THE INVENTION

Figure 1:
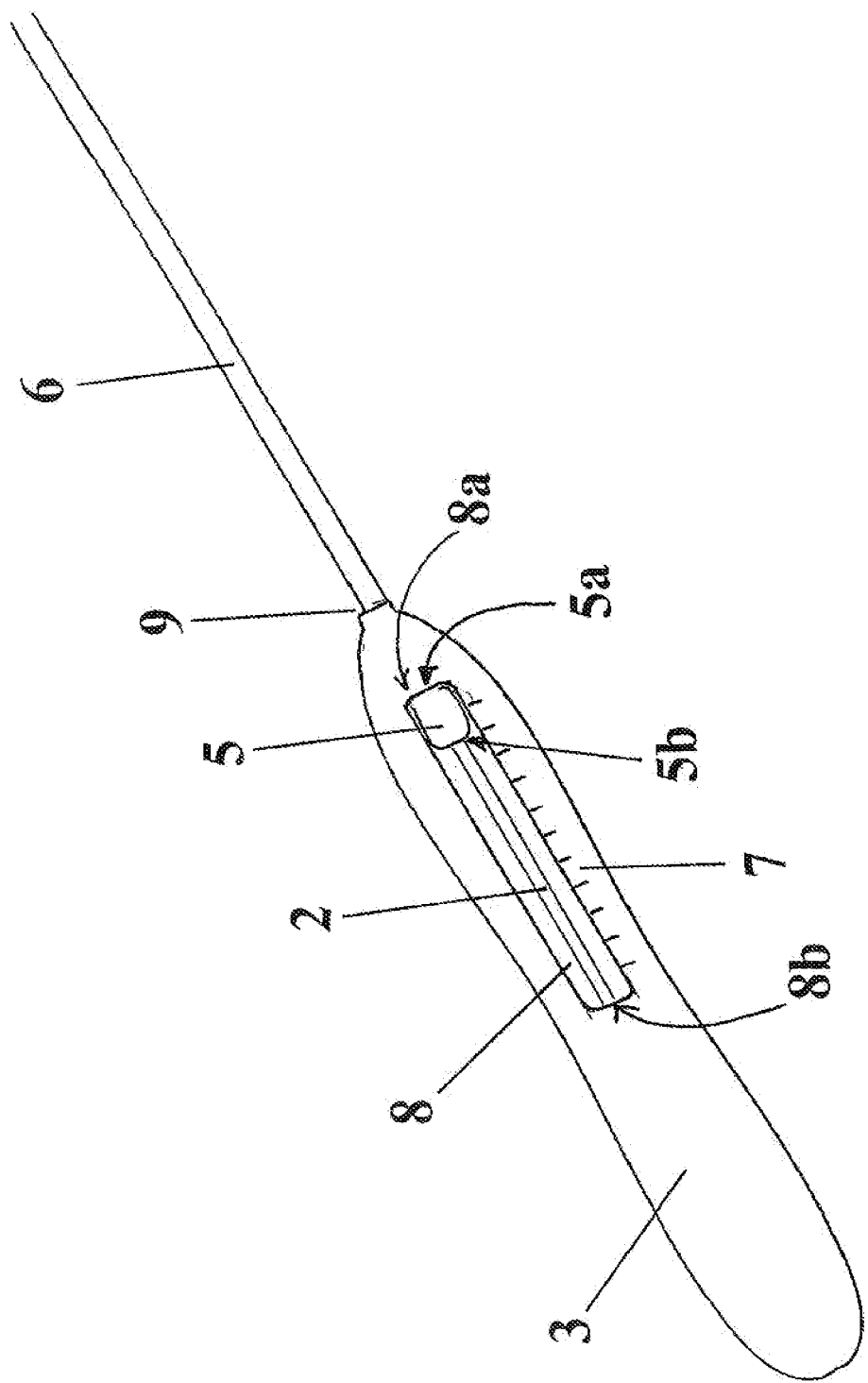
FIG. 1 illustrates a general overview of an inserter according to an embodiment of the invention.

A typical inserter for an intrauterine system according to the present invention, comprises
- a handle having a longitudinal opening at its first end, said opening having a longitudinal axis parallel to the longitudinal axis of the inserter, a first end and a second end,
- a movable slider arranged in said longitudinal opening and having a first end and a second end,
- a plunger attached to the handle and having a longitudinal axis,
- an insertion tube having a first end, a second end and a longitudinal axis essentially parallel to the longitudinal axis of the plunger, the insertion tube being, along said longitudinal axis, movably arranged around the plunger,
- a flange arranged on the insertion tube at its first end.

The inserter is characterized in that it further comprises
- means for locking the slider into a position showing the correct insertion depth for the intrauterine system, said means being adjustable with respect to the opening of the handle.

The invention therefore provides an easy to use inserter, by which only few simple steps are needed to prepare for the insertion and to securely install and position an intrauterine system into the uterus.

The longitudinal opening on the handle can have be also quite narrow and does not need to be symmetrically positioned on the handle and with respect to the longitudinal axis The inserter comprises a flange arranged on the insertion tube at its first end. The aim of this flange is to keep the intrauterine system in a correct position and to protect it prior to insertion. The flange also functions as part of the means regulating the movement of the insertion tube.

The inserter may further comprise means for holding and guiding the strings during the insertion so that no manual handling of said strings will be needed. The inserter may also comprise locking means for reversibly locking the strings to immobilize the intrauterine system in relation to the plunger, said locking means being controllable by the slider and/or by the insertion tube.

The inserter according to the invention is suitable for the positioning of intrauterine devices and intrauterine systems having different sizes and shapes. The inserter is especially suitable for installing intrauterine devices having a flexible frame with continuous curved shape, for example annular, circular, oval, spiral, toroidal, triangular, shield-like, almond-like, diamond-like, elliptical or polygonal shape.

In the present description and claims, by first ends are typically meant the ends that are closer to the uterus during the insertion of the intrauterine system. Second ends are the ends opposite to the first ends. Moreover, the terms IUS or IUD and removal strings are used when describing the preferred embodiment of the present invention, but these are not to be construed as limiting the claims.

A part of the handle comprises an opening having a first end and a second end and running in the longitudinal direction of the plunger. The handle also preferably has at its first end a channel in which the insertion tube can slide in the longitudinal direction.

The handle can have many shapes and is designed for easy handling of the inserter even by using only one hand. The plunger attached to the handle is advantageously hollow or has a groove or bore running in the axial direction thus allowing the string(s) to slide freely in it, without any risk of them getting jammed between the plunger and the insertion tube. To enable the optimal and secure positioning of the intrauterine system in the inserter the forward end of said plunger is shaped to the form of a a slot or an extension to adapt the reservoir of the intrauterine system. Thus the IUS will not drop or be twisted during insertion procedure and assumes a specified constant configuration when released.

The forward part (part directed towards the uterus) of the inserter is preferably made of a flexible material to avoid perforation of the uterus, and can be straight or curved so as to conform to the anatomy of the uterus. The first end of the insertion tube comprises a flange and both are made of a relatively flexible material, but are preferably stiffer than the plunger.

The slider mechanism is preferably inside the handle and comprises at least one elongated element, which can be moved in the longitudinal direction of the insertion tube. According to an embodiment of the invention the slider comprises a means to move the slider, which preferably is a part of the slider. According to another embodiment of the invention the slider comprises at least two elements, preferably parallel, which are combined on at least one point by a transversal member. The transversal member may form means, for example a knob or switch, by which the slider can be moved. The handle can comprise one or more means to adapt the slider elements and to facilitate the movement of the slider, for example a support, a shoulder, a holder, a saddle, a groove or a slot. The slider may also comprise at least one structural element, for example an extension, which is capable to generate the necessary operation of the possible locking means to keep the strings immobilized during storage or during preparatory steps before insertion and/or to release the string(s) when the slider is moved to the backward position.

To ensure the correct positioning of the intrauterine system in the uterus, the slider is adjusted to correspond to the depth at which intrauterine system will be inserted, said depth being beforehand determined by using a sound or a probe. The slider comprising said means for locking it, which means are adjustable with respect to the opening of the handle can be for example a self-locking button slider and movable in a stepwise way controlled for example by an indentation, a cogwheel or a rack and pinion mechanism positioned inside the handle. The outer side of the handle has clear depth markings to facilitate the adjustment of the slider.

The slider and/or the insertion tube may additionally comprise at least one structural element, for example an extension, which is capable to generate the necessary operation of the locking means to keep the strings immobilized during storage or during preparatory steps before insertion or to release the string(s) when the slider is moved to the backward position.

According to an embodiment of the invention relating to the kit comprising also an intrauterine system, a therapeutic component of the intrauterine system is connected to the frame in at least one point. Moreover, the intrauterine system can be connected to the inserter for example via at least one connection part. The connection part is preferably designed such that it enhances the retention of the device on the inserter prior and during the insertion of the device.

The connection part can be for example a hollow knob, adapted to receive a pin, one of these parts being arranged on the intrauterine system and the other on the inserter. Another option is to use a traditional ball joint. A person skilled in the art is readily able to find a suitable solution for this connection part.

Also in view of this, and according to an embodiment of the invention, the first end of the plunger comprises at least one connection slot for receiving the connection part of the intrauterine system. The first end of the plunger may also comprise two diagonally symmetrical connection slots for receiving the connection part of the intrauterine system. It is naturally possible that there are more than two connection slots, such as three, four, five or six slots. The connection part then preferably comprises suitable parts fitting to these connections slots.

According to another embodiment of the invention, the first end of the plunger comprises at least one frame slot for receiving the frame of the intrauterine system. The first end of the plunger may also comprise two diagonally symmetrical frame slots for receiving the frame of the intrauterine system. The number of frame slots can also be higher, such as three, four, five or six. The frame slots can be parallel to the longitudinal axis of the plunger or non-parallel to it. The frame slots can for example be straight or slightly curved with respect to the outer surface of the plunger, in order for allowing the frame to be released. The frame slots are preferably narrow enough to prevent the therapeutic component from slipping out and long enough to allow the movement of the therapeutic component and the stretching/compression of the frame during the insertion step. The plunger or at least the first end of the plunger is large enough for containing the therapeutic component. The frame slot(s) together with connection parts and the flange assure that the intrauterine system will be securely fitted and in the correct configuration during the insertion.

According to a further embodiment of the invention, the first end of the insertion tube comprises at least one frame slot for receiving the frame of the intrauterine system. The first end of the insertion tube may also comprise two diagonally symmetrical frame slots for receiving the frame of the intrauterine system. The number of frame slots can also be higher, such as three, four, five or six. The frame slots can be parallel to the longitudinal axis of the insertion tube or non-parallel to it. The frame slots can for example be straight or slightly curved with respect to the outer surface of the insertion tube, in order for allowing the frame to be released. The frame slots are preferably narrow enough to prevent the therapeutic component from slipping out and long enough to allow the movement of the therapeutic component and the stretching/compression of the frame.

The inserter according to the present invention may also comprise locking means for reversibly locking the intrauterine system in relation to the plunger, said locking means being controllable by the slider and/or the insertion tube. This means that the locking means can also be controlled by a part of the slider and/or of the insertion tube, such as an extension of either or both of them. The locking means is any arrangement which, induced by the movement of the slider, of the means to move the slider or of the insertion tube, can immobilize the removal string(s) to held IUS in stable position and again unlock the string(s) after insertion to release the IUS. Particularly, the invention relates to a locking means which comprises an object capable of reversibly preventing the movement of the string(s) by at least partly moving or pivoting from the original position, for example rotating around a shaft or an axle, and vertically or horizontally attached to the handle. The object may have several shapes and may be for example round or rod-shaped, wedge, polygonal or rectangular with rounded or sharp corners. The surface of the object preferably comprises one or more extensions having variable size and shape, for example a knob, a rib or a switch.

When the slider mechanism is pressed down and moved to adjust the correct insertion depth a part or an extension of the slider is pressed against at least one extension of the object thus changing its orientation enough relative to the original position to cause release of the string(s). As soon as the slider is released, the strings will lock again.

Preferably the object has a slot or pinhole through which the string(s) run. The locking means may also comprise at least one counterpart against which the string(s) are pressed by the object and thus reversibly immobilized in the locking position. The counterpart has a suitable shape adapted to fit at least some part of the surface of the object. An extension, or extensions of the object can be used to keep the object and the counterpart in a fixed configuration until the IUS is released. The counterpart preferably has a suitable design to keep the string(s) in proper direction, for example a slot or pinhole through which the string(s) run. Further, the object and said at least one counterpart have preferably a suitable length and diameter to fit inside the handle.

As an alternative or in addition to the locking means, the outer surface of the insertion tube or the handle can have means to hold the strings until the intrauterine system has been inserted.

According to one embodiment of the invention, the locking means thus comprises
  a main part,
  a first extension of the main part having an abutment surface,
  a counterpart adapted to form a blocking together with the main part,
wherein the locking means is rotatably mounted on the inserter.

According to another embodiment of the invention the main part comprises an opening or a slot in a diagonal direction through essentially the whole diameter of the main part, adapted to receive at least one removal string of the intrauterine system.

According to yet another embodiment of the invention, the locking means comprises
  a main part,
  a first extension of the main part having an abutment surface,
  a second extension of the main part having a wedge-like shape,
  a counterpart adapted to form a blocking together with the main part, wherein the second extension is adapted to form a blocking together with the counterpart and the locking means is rotatably mounted on the handle of the inserter.

According to one embodiment of the invention, the main part has essentially the shape of a cylinder, or it is of triangular shape, or of any other suitable shape.

According to one embodiment of the invention the insertion tube comprises an extension adapted to abut on the abutment surface of the first extension of the main part of the locking means.

According to one other embodiment of the invention the locking means comprises a main part comprising a first extension and a second extension arranged, in their initial position, to be essentially in contact with each other to from a blocking, wherein a part of the slider, the insertion tube or a part of the insertion tube is arranged to protrude into the main part of the locking means so as to separate the first and second extensions from each other.

According to yet one other embodiment of the invention the locking means comprises
- a first locking part and a second locking part movably mounted on the inserter and arranged, in their initial position, to be essentially in contact with each other to form a blocking, and
- a first protrusion and a second protrusion arranged on the inner surface of the outer insertion tube, wherein the first and second protrusions are arranged to move the first and second locking parts when moving the outer insertion tube.

The locking means could also be welding, gluing, cutting, knot or adhesion. The strings could thus be for example attached to the body of the inserter by welding (for example by heating), gluing with glue or attaching with an adhesive agent (such as sticker). The insertion tube would then release the attachment when contacting the slider. Other options could be a knot or other mechanical hindrance, when the slot provided for the strings is larger in the releasing position. The insertion tube could also comprise a blade that cuts the strings away from the inserter.

It is obvious to a person skilled in the art that, in accordance with the above description, the locking means can be of any other kind than those specifically listed above as well as a combination thereof.

During the preparatory steps the string(s) are hold tightly or locked but they are released automatically, when the slider is moved for example to adjust the insertion depth or when the second end of the insertion tube meets the slider or when the inserter is drawn out after insertion in order to release the IUS. As compared to previous inserters there is no need to manually handle the removal strings during the preparatory steps and during insertion, which increases security and hygiene and eliminates the possibility of user-made mistakes. Moreover, during the insertion the plunger and the medical device are protected by the insertion tube up to the cervix, which also increases hygiene. The invention further relates to a kit comprising an intrauterine system and an inserter according to the present invention. The intrauterine system can be any intrauterine system known in the art. Any details and embodiments listed above naturally apply mutatis mutandis to the kit according to the invention.

The present invention also relates to a method for positioning an intrauterine system in a uterus of a patient, wherein the method uses an inserter according to the present invention. The method comprises the steps of
- sounding the depth of the uterus to obtain the correct positioning depth,
- moving the slider mechanism towards the second end of the opening until its position corresponds to said positioning depth, as shown by the depth markings of the handle,
- introducing the inserter into the uterus of the patient until the flange on the insertion tube abuts the cervical opening,
- introducing the plunger with the intrauterine system further into the uterus until the insertion tube meets the slider while moving backwards away from the uterus, which shows that the intrauterine system is in its correct location,
- removing the inserter from the uterus of the patient.

An example of the method for positioning the intrauterine system is given hereafter. To insert the IUS only few steps are needed. To prepare for the insertion the sterile package is carefully opened. The IUS is in a correct configuration relative to the inserter and there is no need to align the intrauterine system or for example to rearrange or correct the frame. The IUS is positioned at the forward end of the plunger with the reservoir of the intrauterine system protected by the extension of the plunger and the frame locating outside the plunger in the expanded configuration, secured and protected by the flange. The removal string(s) attached to the intrauterine system are preferably immobilized by the locking means, by the means on the surface of the insertion tube, or by both, to keep the IUS at a steady and correct position until it is released in the uterus. The removal strings do however not necessarily need to be immobilized.

Prior to the insertion procedure the depth of the uterus is measured by sounding. The slider mechanism or the means to move the slider is moved to correspond to the correct sounding depth. In the simplest form the slider is equipped with a self-locking press down and slide back button to adjust the correct sounding depth.

Then, the handle is hold tightly and the inserter is introduced into the uterus until the flange touches the cervical opening. At this point the insertion tube starts moving backwards and the flexible plunger with the intrauterine system will go forwards into the uterus. The insertion is continued until the insertion tube meets the slider, when also the removal string(s), if locked, are released by the locking means or by the means on the insertion tube. At this point IUS is in the correct location, as determined beforehand by using a sound as described above.

The inserter thus allows easy and secure positioning of an IUS. The use of the slider mechanism is straightforward and the locking means to hold the string(s) and the IUS immobile long enough as well as the predetermined distances the insertion tubes can be moved in each step guarantee an accurate positioning of the IUS during insertion and its accurate release.

DETAILED DESCRIPTION OF THE DRAWING

In the following description, the term slider and the corresponding reference number are used to designate both the slider itself and the means to move the slider attached to the slider. The term slider is used for convenience of reading.

FIG. 1 illustrates a general overview of an inserter according to the invention. The inserter comprises a handle 3, a plunger 2 attached to the handle, a slider having means to move the slider 5, an insertion tube 6 around the plunger, an IUS and the string or strings (not shown here) for the removal of the IUS, means for reversibly locking the string (s) (not shown) in such a way that the IUS remains immobile in relation to the plunger during the necessary steps prior to and during insertion, and again for releasing the string(s) and the IUS after it has been inserted, an opening 8, a channel 9 in which the insertion tube slides in the longitudinal direction, and depth markings 19 on the handle which are used to adjust the slider to correspond the depth of the uterus.

In this case the forward part of the handle 3 forms an opening 8, having the first end 8a and the second end 8b, which opening runs in the direction of the plunger 2 and has at the first end a channel 9 in which the insertion tube 6 slides in the longitudinal direction. The front surface of the means to move the slider 5a is set on the depth marking corresponding the depth of the uterus, i.e. the insertion depth, as determined before hand by using a sound or a probe.

FIGS. 2A, 2B, 2C and 2D illustrate an operating principle of the inserter.

Figure 2A:
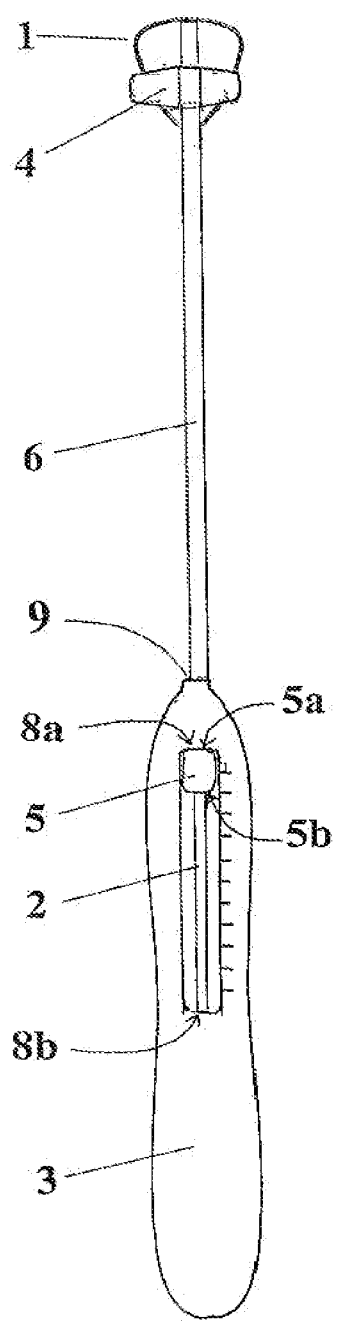
FIGS. 2A, 2B, 2C and 2D illustrate an operating principle of an inserter according to an embodiment of the invention.

FIG. 2A shows an inserter and in this case an almond-shaped IUS 1 in a configuration as they are in the sterilized package. The IUS is placed in the front end (entry into the uterus) of the inserter so that the elongate member of the intrauterine system or the elongated member with a drug containing reservoir is inside the head of the plunger and the frame of the intrauterine system is in the expanded configuration and partly covered by the flange 4. The means to move the slider 5 is on the basic position. The removal string(s) are inside the inserter, tightened and locked by the locking means (not shown in the Figure) or outside under the insertion tube hold by suitable means or extensions.

Figure 2B:
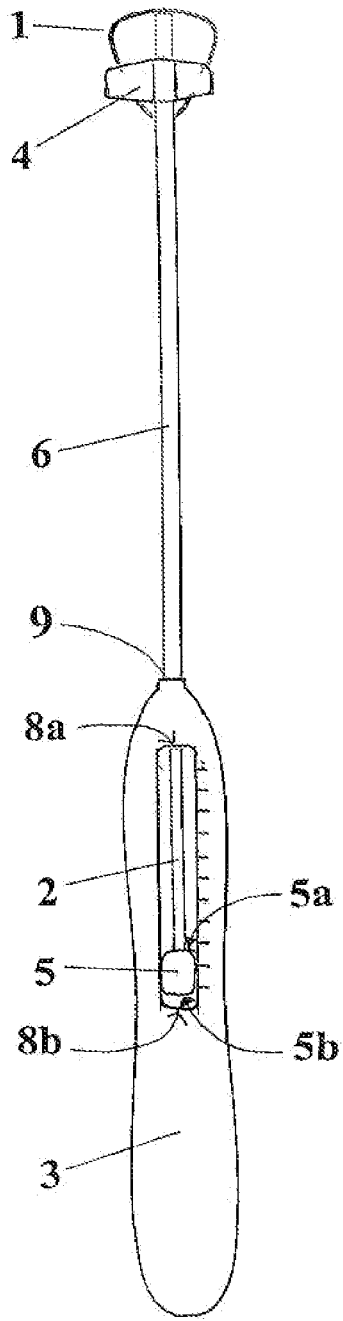

FIG. 2B illustrates the first step of insertion procedure. After the insertion depth has been determined by sounding, the slider is moved backwards until surface 5a is on a correct depth marking of the handle 3.

Figure 2C:
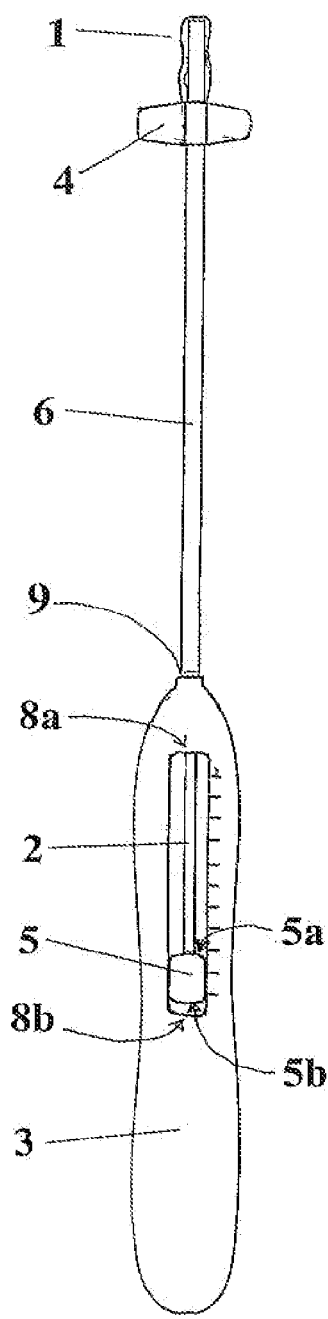

FIG. 2C illustrates the procedure to insert the IUS. The intrauterine system in the configuration according to FIG. 2B is gently introduced into the uterus until the flange abuts the cervical opening. The frame of the IUS will compress against the head of the plunger.

Figure 2D:
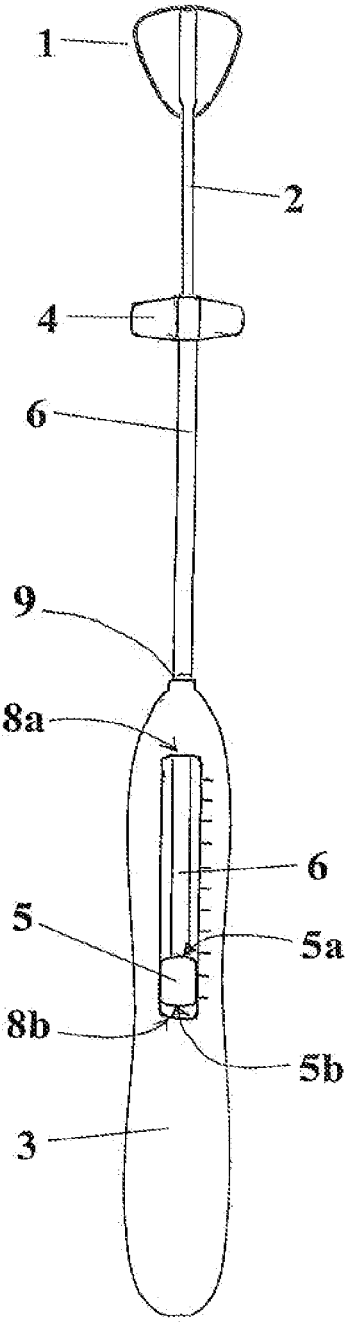

FIG. 2D illustrates the final step of insertion procedure. Insertion is continued from the step of FIG. 2C. The flange pressed against the cervical opening will cause the insertion tube to move backwards, and only the plunger with the intrauterine system will move towards the uterus. The insertion tube will move until the rear end of the tube meets the slider and at this point the intrauterine system is correctly positioned in the uterus. The inserter is retracted out of the uterus. The strings and the intrauterine system are automatically released when the insertion tube meets the slider or when the inserter is drawn out. The distance the insertion tube can move has been selected to indicate clearly the moment at which the IUS has completely been positioned.

Figure 3A:
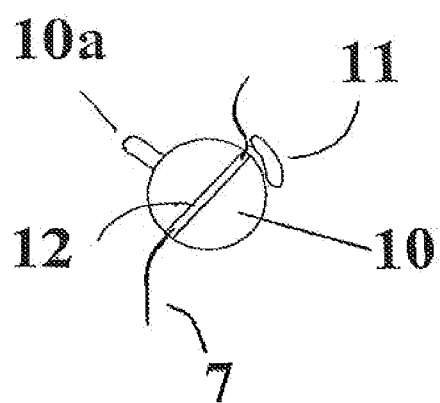
FIGS. 3A and 3B illustrate a locking means according to an embodiment of the invention.
Figure 3B:
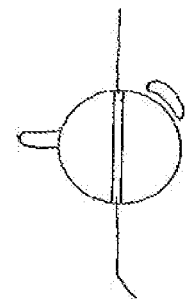

FIGS. 3A and 3B illustrate a locking means according to an embodiment of the invention. The locking means are arranged preferably at the inside of the handle 3, on any of the inside surfaces of the handle. The locking means are used to immobilise and release the string(s) of the IUS.

FIG. 3A illustrates a locking means according to an embodiment of the invention comprising a main part 10 having essentially the shape of a cylinder and comprising an opening 12 there through in a diagonal direction. The string(s) 7 of the IUS pass through the opening 12. The main part 10 is rotatably mounted on the handle, on a shaft or an axle (not shown). The locking means also comprises a counterpart 11, such that in the locking position the string(s) are immobilized between the counterpart and the main part. The counterpart thus has a suitable shape adapted to fit to a part of the surface of the main part. When the slider is moving backwards, at a suitable point a part or an extension of the slider is pressed against the extension 10a of the main part 10 thus turning it enough to release the string(s), as shown in FIG. 3B.

Figure 4A:
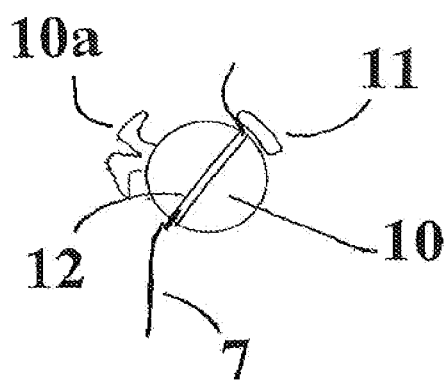
FIGS. 4A and 4B illustrate a locking means according to another embodiment of the invention.
Figure 4B:
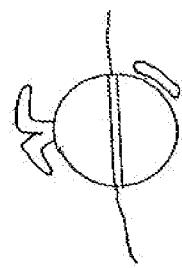

FIGS. 4A and 4B illustrate a locking means according to another embodiment of the invention. FIG. 4A illustrates an object similar to the one presented in FIG. 3A, but having a different construction of the extension 10a.

Figure 5A:
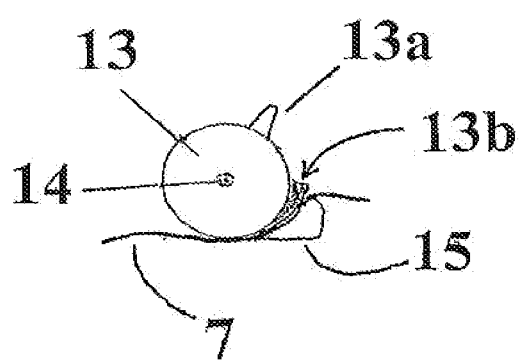
FIGS. 5A and 5B illustrate a locking means according to yet another embodiment of the invention.
Figure 5B:
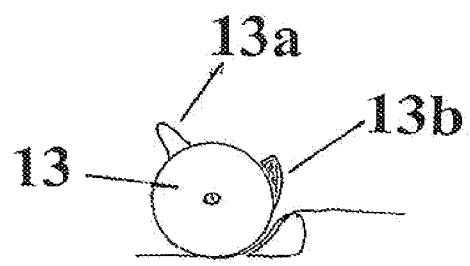

FIGS. 5A and 5B illustrate a locking means according to yet another embodiment of the invention. This is a side view of a cylindrically shaped locking means, having a main part 13 which comprises two extensions 13a and 13b. The locking means can rotate around a shaft or an axle 14 and is preferably attached to a shorter side of the inner surface of the handle. The locking means also comprises a counterpart 15 such that the string(s) 7 are immobilised between the counterpart 15 and the extension 13b. The counterpart 15 has a suitable shape adapted to fit to a part of the surface of the extension 13b. When the slider is moving backwards, at a suitable point a part or an extension of the slider is pressed against the extension 13a thus turning it enough to release the string(s), as shown in FIG. 5B. In this case the handle can also comprise a groove in which the string(s) run (not shown).

Figure 6A:
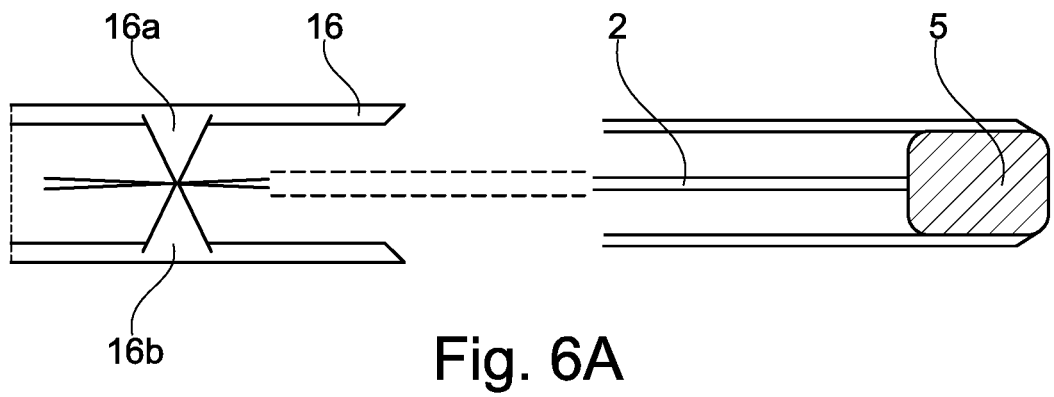
FIGS. 6A and 6B illustrate a locking means according to a further embodiment of the invention.
Figure 6B:
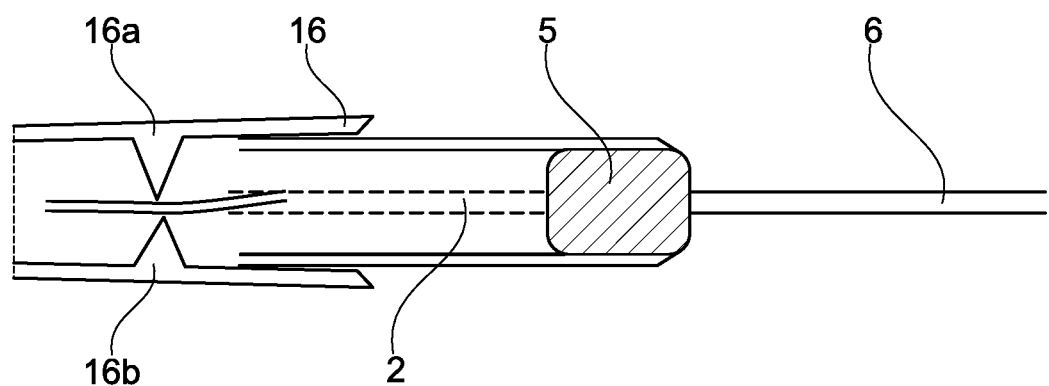

FIGS. 6A and 6B illustrate a locking means according to an embodiment of the invention. The locking means 16 comprises two extensions 16a and 16b to immobilize the strings as shown in FIG. 6A. When the slider 5 and the insertion tube 6 move backwards the slider and/or the insertion tube protrudes into the locking means at least partly to expand the means enough to separate the extensions and to release the strings, as shown in FIG. 6B.

Figure 7A:
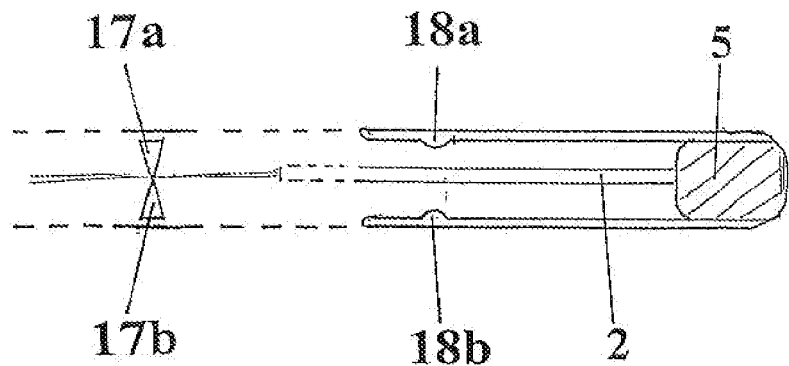
FIGS. 7A and 7B illustrate a locking means according to still a further embodiment of the invention.
Figure 7B:
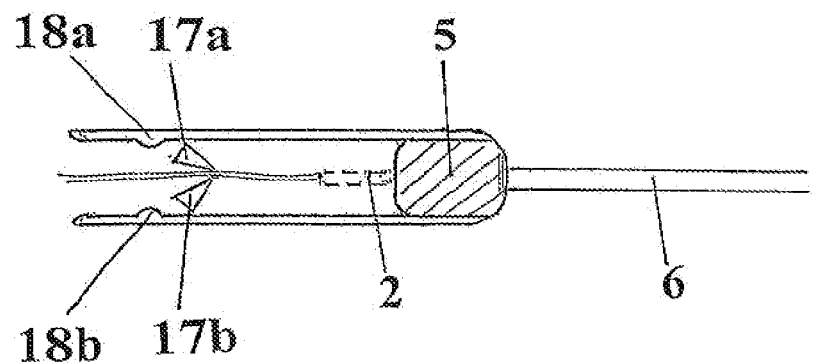

FIGS. 7A and 7B illustrate a locking means according to a further embodiment of the invention. The locking means comprises two parts 17a and 17b to immobilize the strings as shown in FIG. 7A, said parts being able to move or turn from the original position. The slider 5 has two extensions 18a and 18b. When the slider 5 and the insertion tube 6 move backwards the slider extensions turn the locking parts 17a and 17b apart from each other enough to release the strings, as shown in FIG. 7B.

Figure 8A:
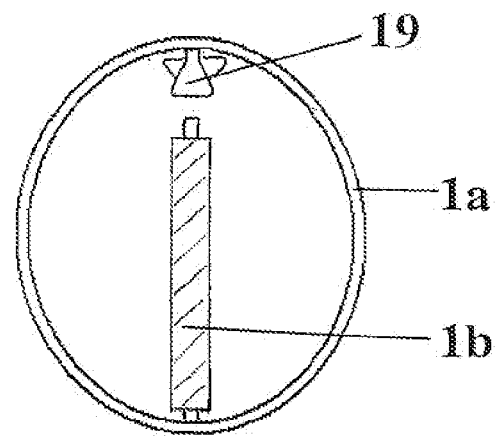
FIGS. 8A and 8B illustrate an intrauterine system and its positioning on the inserter according to an embodiment of the invention.
Figure 8B:
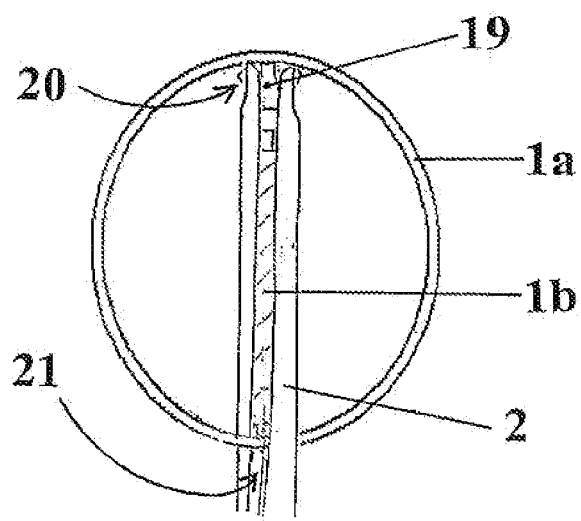

FIGS. 8A and 8B illustrate an intrauterine system and its positioning on the inserter according to an embodiment of the invention. The intrauterine system has a frame 1a and a therapeutic component 1b and it is positioned in the plunger or in an extension of the plunger 2. The intrauterine system is connected to the inserter via one connection part 19. The first end of the plunger 2 comprises one connection slot 20 for receiving the connection part 19. The therapeutic component is essentially completely and the frame essentially only partly positioned in a frame slot 21.

Figure 8C:
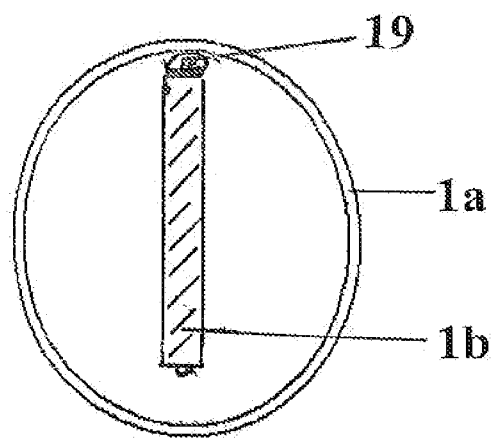
FIGS. 8C and 8D illustrate another intrauterine system and its positioning on the inserter according to an embodiment of the invention.
Figure 8D:
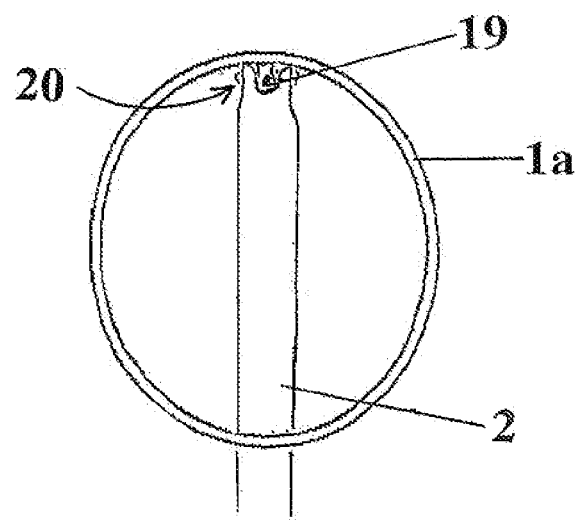

FIGS. 8C and 8D illustrate another intrauterine system and its positioning on the inserter according to an embodiment of the invention, which has the same parts 1a, 1b, 2, 19 and 20 as in FIGS. 8A and 8B. In this embodiment, the therapeutic component is essentially completely positioned inside the plunger and the frame is essentially completely outside the plunger.

Figure 9A:
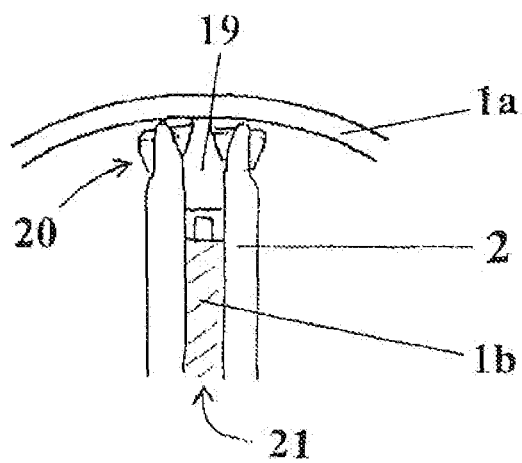
FIGS. 9A and 9B illustrate some details of FIG. 8B.
Figure 9B:
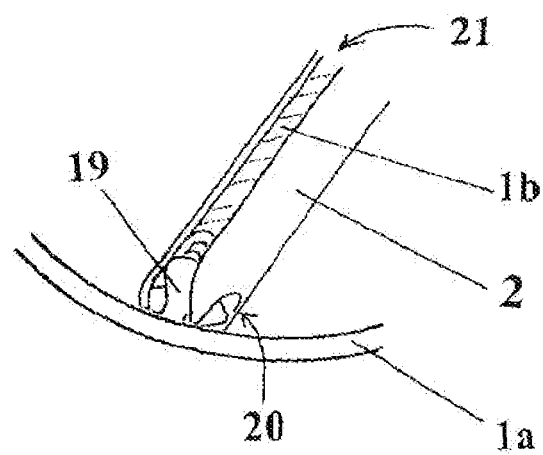

FIGS. 9A and 9B illustrate some details of FIG. 8B, namely the first end of the plunger 2 and the connection of the intrauterine system on the plunger.

The invention claimed is:
1. An inserter for an intrauterine system comprising:
 a handle having a longitudinal opening at its first end, the longitudinal opening having a longitudinal axis parallel to the longitudinal axis of the inserter, a first end and a second end;

a movable slider arranged in the longitudinal opening and having a first end and a second end;

a plunger attached to the handle and having a longitudinal axis;

an insertion tube having a first end, a second end and a longitudinal axis essentially parallel to the longitudinal axis of the plunger, the insertion tube being, along the longitudinal axis, movably arranged around the plunger; and a lock comprising two locking parts that include a triangular shape with points that immobilize a removal string, wherein turning or moving the two locking parts causes the points to move towards each other.

2. The inserter of claim 1, wherein:

the movable slider comprises a first extension and a second extension; and wherein moving the movable slider backwards causes the first extension and the second extension to turn or move the two locking parts apart from each other to release the removal string.

3. The inserter of claim 2, wherein the first extension and the second extension are rounded protrusions on the movable slider.

4. The inserter of claim 1, further comprising:

a flange arranged on the insertion tube at its first end, wherein the flange is arranged to be in contact with the intrauterine system and surround the intrauterine system before its insertion.

5. The inserter of claim 1, wherein the first extension and the second extension hold and guide the removal strings of the intrauterine system during its insertion.

6. A kit comprising an intrauterine system and the inserter of claim 1.

* * * * *